United States Patent [19]

Sherba et al.

[11] Patent Number: 5,227,360
[45] Date of Patent: Jul. 13, 1993

[54] SYNERGISTIC ANTIALGAL COMPOSITIONS COMPRISING DIPHENYLETHERS AND CERTAIN COMMERCIAL BIOCIDES AND SWIMMING POOL LINER COMPOSITIONS COMPRISING THE ANTIALGAL COMPOSITIONS

[75] Inventors: Samuel E. Sherba, Willingboro, N.J.; Terry M. Williams, Ambler; Gary L. Willingham, Glenside, both of Pa.

[73] Assignee: Rohm and Haas Company, Philadelphia, Pa.

[21] Appl. No.: 926,270

[22] Filed: Aug. 5, 1992

Related U.S. Application Data

[62] Division of Ser. No. 656,905, Feb. 15, 1991, Pat. No. 5,158,596.

[51] Int. Cl.⁵ .............. A01N 31/14; A01N 43/50; A01N 57/20; A01N 55/02
[52] U.S. Cl. .................... 504/152; 504/153; 504/156; 504/157; 504/161; 523/122; 4/488
[58] Field of Search ............. 504/152, 153, 156, 157, 504/161

[56] References Cited

U.S. PATENT DOCUMENTS

| | | | |
|---|---|---|---|
| 4,854,961 | 8/1989 | Wellinga et al. | 71/88 |
| 4,925,866 | 5/1990 | Smith | 514/389 |
| 4,975,111 | 12/1990 | Woodruff et al. | 71/67 |

FOREIGN PATENT DOCUMENTS 2800105 7/1978 Fed. Rep. of Germany.

Primary Examiner—Allen J. Robinson
Assistant Examiner—S. Mark Clardy
Attorney, Agent, or Firm—Michael B. Fein

[57] ABSTRACT

Synergistic antialgal compositions comprising substituted fluoroalkyl diphenylethers and a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly[oxyethylene(dimethylimino)ethylene(dimethylimino)ethylene dichloride], 3-iodo-2-propynylbutylcarbamate, sodium N-methyldithiocarbamate, 3-(3,4-dichlorophenyl)-1,1-dimethylurea, N-(phosphonomethyl)glycine and salts thereof, zinc bis(dimethyldithiocarbamate), p-tolydiiodomethylsulfone and fatty acid salt in ratios to each other which exhibit synergism are disclosed. Particularly effective combinations are based on oxyfluorfen as the diphenylether for use in protecting aqueous systems, such as latices and cooling water systems, from algal growth.

2 Claims, No Drawings

SYNERGISTIC ANTIALGAL COMPOSITIONS COMPRISING DIPHENYLETHERS AND CERTAIN COMMERCIAL BIOCIDES AND SWIMMING POOL LINER COMPOSITIONS COMPRISING THE ANTIALGAL COMPOSITIONS

This is a divisional of application Ser. No. 656,905, filed Feb. 15, 1991 now U.S. Pat. No. 5,158,596.

BACKGROUND OF THE INVENTION

1. Field of the Invention

The present invention relates to antialgal compositions, methods of controlling algae, and coating compositions comprising the antialgal compositions.

2. Description of the Prior Art

The presence of algae in various aqueous systems such as latices, paints, coatings, cooling water systems, decorative ponds and the like, can cause deterioration or disfigurement of these systems. For example, painted surfaces may be disfigured by the unsightly buildup of algae, thus detracting from the overall aesthetics of the painted article; cooling towers may lose efficiency due to the buildup of algae on surfaces, thus reducing the heat transfer capabilities of the tower. It is conventional to practice methods which inhibit the algal deterioration of such systems by incorporating a variety of additives or combination of additives that are characterized by having antialgal activity.

A wide variety of materials have been used to control algae in different environments, some of which are: chlorine/bromine compounds, glutaraldehyde, isothiazolones, organotin formulations, copper salts, quaternary ammonium compounds (SD Strauss and PR Puckorius in *J. Power*, S1, June 1984), and triazines. Each has deficiencies related to toxicity, pH and temperature sensitivity, limited effectiveness, chemical stability, and/or compatibility.

European patent application EP 384661A discloses the use of diphenylethers in antialgal compositions, and U.S. Pat. No. 4,975,111 discloses the use of said diphenylethers with isothiazolones as antialgal compositions.

European patent application EP 143547A teaches the use of oxyfluorfen diphenylether/glyphosate (N-(phosphonomethyl)glycine) mixtures as having enhanced herbicidal activity towards weeds and grasses.

Oxyfluorfen in combination with diuron (3-(3,4-dichlorophenyl)-1,1-dimethylurea) has been found to be an effective herbicide for weed control in sugarcane fields (HJ Yeh, *Taiwan Sugar*, 27(4), 125–129, 1980), nectarine crops (MJ Hartley, Proc. N.Z. *Weed Pest Control Conf.*, 40th, 140–143, 1987), and biomass production (P Felker and CE Russell, *J. Hortic. Sci.*, 63(1), 149–155, 1988).

Based on the aforementioned performance deficiencies of conventional antialgal compounds there is a need for more effective antialgal agents that can be used at lower dosage rates, thus being more cost effective for the end user, reducing the pollution load on the affected environmental systems, and reducing the side effects to nearby non-target organisms, such as fish, useful crops, etc.

SUMMARY OF THE INVENTION

It is an object of this invention to provide a method of controlling algae at very low levels of active ingredient. It is a further object to use compositions which are compatible with a variety of systems susceptible to deterioration by algae. Another object is to provide a method of controlling algae in cooling towers, paints, marine antifoulant coatings, spray washes (e.g., algicidal washes or air-washer systems), swimming pools, coatings, decorative ponds and the like, without objectionable by-product odors, discoloration, or otherwise detrimental effects on the treated (and controlled) systems. These objects, and others which will become apparent from the following disclosure, are achieved by the present invention which is, in one aspect a composition useful for controlling algae comprising (A) a diphenylether compound of the formula

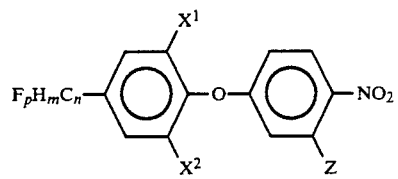

wherein
- $X^1$, $X^2$ are independently selected from hydrogen, halogen, trihalomethyl, cyano, or $(C_1-C_4)$alkyl, and
- Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or substituted lower alkyl amino, RO in which R represents a hydrogen atom or an ester bonded acid radical of an inorganic or organic oxyacid;
- p is an integer from 1 to $2n+1$;
- m is an integer of 0 to $2n$;
- n is an integer of 1 to 5;
- $m+p=2n+1$ and (B) a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly[oxyethylene(dimethylimino)ethylene(dimethylimino)ethylene dichloride], 3-iodo-2-propynylbutylcarbamate, sodium N-methyldithiocarbamate, zinc bis(dimethyldithiocarbamate), p-tolydiiodomethylsulfone and fatty acid salt.

In another aspect, the invention comprises a method for inhibiting the growth of algae in a locus subject to contamination by algae, which comprises incorporating onto or into the locus, a composition comprising the aforementioned diphenylethers and a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly[oxyethylene(dimethylimino)ethylene(dimethylimino)ethylene dichloride], 3-iodo-2-propynylbutylcarbamate, sodium N-methyldithiocarbamate, zinc bis(dimethyldithiocarbamate), p-tolyldiiodomethylsulfone, 3-(3,4-dichlorophenyl)-1,1-dimethylurea, N-(phosphonomethyl)glycine and salts thereof, and fatty acid salt in an amount which is effective to adversely affect the growth of algae.

Another aspect of the invention is a method of controlling algae in cooling tower water comprising maintaining a concentration of the aforementioned composition in the water.

In another aspect, the invention comprises a method of imparting algal resistance to a coating or impregnant composition comprising incorporation of the antialgal composition in the coating or impregnant.

The invention also comprises algae-resistant coating or impregnant compositions and marine antifoulant compositions comprising the antialgal composition.

DETAILED DESCRIPTION OF THE INVENTION AND THE PREFERRED EMBODIMENTS

We have discovered an especially effective composition useful for controlling algae comprising (A) a diphenylether compound of the formula

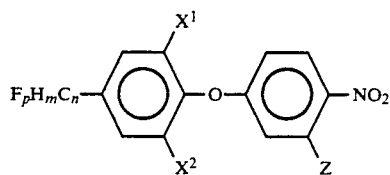

wherein
$X^1$, $X^2$ are independently selected from hydrogen, halogen, trihalomethyl, cyano, or $(C_1-C_4)$alkyl, and Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or substituted lower alkyl amino, RO in which R represents a hydrogen atom or an ester bonded acid radical of an inorganic or organic oxyacid;

p is an integer from 1 to 2n+1;
m is an integer of 0 to 2n;
n is an integer of 1 to 5;
m+p=2n+1 and (B) a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly[oxyethylene(dimethylimino)ethylene(dimethylimino)ethylene dichloride], 3-iodo-2-propynylbutylcarbamate, sodium N-methyldithiocarbamate, zinc bis(dimethyldithiocarbamate), p-tolyldiiodomethylsulfone and fatty acid salt.

Where the expression "lower" is employed in conjunction with terms, such as alkyl, alkoxy, etc., it is intended to indicate that the alkyl or alkyl portion thereof has 1 to 6 carbon atoms, i.e., $(C_1-C_6)$.

More preferred are compositions wherein said compound (A) is of the formula

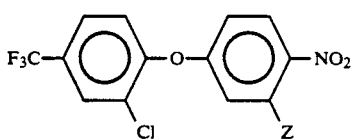

wherein Z is selected from the group consisting of alkoxy, carboxy or salt thereof, carbalkoxyalkoxy, and —$CO_2CH_2CO_2C_2H_5$.

The most preferred embodiment of compound (A) is oxyfluorfen which has the formula

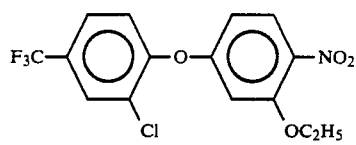

The materials (commercial biocides) which were found to be useful for algicidal compositions in combination with diphenylethers are described below:

sodium hypochlorite (aqueous bleach)
halodialkylhydantoin (bromo-chloro-5,5-di($C_1-C_3$)alkylhydantoins, dichloro-5,5-di($C_1-C_3$)alkylhydantoin, dibromo-5,5-di($C_1-C_3$) alkylhydantoin and the like)
n-alkyl dimethyl benzylammonium chloride (n-($C_1-C_4$)alkyl dimethyl benzyl ammonium chlorides, e.g., trimethyl benzylammonium chloride, dodecyl dimethyl benzylammonium chloride and the like)
2,2-dibromo-3-nitrilopropionamide
2-bromo-2-nitro-1,3-propanediol
poly[oxyethylene(dimethylimino)ethylene(dimethylimino)ethylene dichloride]
3-iodo-2-propynylbutylcarbamate
sodium N-methyldithiocarbamate
zinc bis(dimethyldithiocarbamate)
p-tolyldiiodomethylsulfone
3-(3,4-dichlorophenyl)-1,1-dimethylurea
fatty acid salt mixture (sodium, potassium salts and the like)
N-(phosphonomethyl)glycine and $(C_1-C_3)$alkylamine and tri$(C_1-C_3)$ alkylsulfonium salts thereof (isopropylamine salt, trimethylsulfonium salt and the like Suitable fatty acid salts include sodium, potassium salts and the like, of alkyl carboxylic acids where the alkyl chain is $(C_2-C_{21})$alkyl, for example butyric ($C_3$-alkyl), lauric ($C_{11}$-alkyl), palmitic ($C_{15}$-alkyl), or stearic ($C_{17}$-alkyl) acids; and unsaturated alkyl carboxylic acids such as oleic, linoleic, and linolenic acids ($C_{17}$)alkyl, and the like.

In accordance with the invention a method of controlling algae comprises using an effective amount of the aforementioned composition.

An especially useful aspect of the invention is in controlling algae in cooling tower water, and in a preferred embodiment, it is maintaining a concentration of about 0.005 to about 20 ppm of the antialgal composition in the cooling tower water, preferably a concentration of about 0.1 to 10 ppm, and most preferably a concentration of about 0.2 to 2 ppm.

Another important utility is in imparting algal resistance to a coating or impregnant composition comprising incorporation of the composition of the invention in the coating or impregnant, preferably at a concentration of about 0.1 ppm to about 2 percent, more preferably at concentration of about 1 ppm to 1 percent, and most preferably at a concentration of about 10 to 4000 ppm.

Algae-resistant coating or impregnant compositions provided by the invention preferably comprise about 0.1 ppm to about 2 percent of the antialgal composition, more preferably about 10 to 4000 ppm.

In a marine antifoulant composition, on the other hand, the antialgal composition of the invention comprises about 1 to 15 percent of the antifoulant composition.

In the protection of fabric, leather, paper or wood materials, the microbicidal composition is added at a concentration of from about 0.1 ppm to about 2 percent by weight. In aqueous media, the microbicidal composition comprises from about 0.1 ppm to about 1 percent of the aqueous system depending on the specific end use; for example, in cooling water tower applications, in the protection of solid surfaces by the application of algicidal washes and with pulp or paper manufacturing processes, the microbicidal composition is added at a concentration from about 0.01 to about 20 ppm by weight.

The algal resistant compositions can also be used in construction products such as stucco, roof mastics, wall mastics, and masonry coatings for algae protection; in clear finishes and coatings to protect underlying substrates from algae; for algae control in aquaculture, including aquaria, fish hatcheries, shrimp ponds, finfish ponds, mollusc and crustacean cultivation; for algae control in recreational and decorative bodies of water such as swimming pools, lakes, fountains and decorative ponds; for algae control in bodies of water for industrial or municipal use, such as settling or separation ponds, waste treatment ponds, spray ponds, water treatment ponds and water reservoirs; for algae control in hydroponic farming; for algae control in processing and manufacture of pulp and paper products; for inclusion in plastics or in coatings for plastics to protect against algae; and in plastics or coatings for plastics for swimming pool liners.

We prefer antialgal compositions wherein the weight ratio of (A) to (B) is from about 1/1000 to about 200/1; more preferably the ratio of (A) to (B) is from about 1/500 to about 100/1. In particular, when (A) is oxyfluorfen, the preferred weight ratios of (A) to (B) are from about 1/20 to about 1/1 when (B) is sodium hypochlorite, 1/100 to about 5/1 when (B) is halodialkylhydantoin, 1/50 to about ½ when (B) is n-alkyl dimethyl benzylammonium chloride, 1/1000 to about 2/1 when (B) is 2,2-dibromo-3-nitrilopropionamide, 1/200 to about 1/20 when (B) is 2-bromo-2-nitro-1,3-propanediol, 1/100 to about 1/5 when (B) is poly[oxyethylene(dimethyliminio)ethylene(dimethyliminio)ethylene dichloride], 1/200 to about ½ when (B) is 3-iodo-2-propynylbutylcarbamate, 1/100 to about 200/1 when (B) is sodium N-methyldithiocarbamate, 1/200 to about 50/1 when (B) is zinc bis(dimethyldithiocarbamate), 2/1 to about 50/1 when (B) is p-tolyldiiodomethylsulfone, 1/10 to about 50/1 when (B) is 3-(3,4-dichlorophenyl)-1,1-dimethylurea, 1/1 to about 50/1 when (B) is N-(phosphonomethyl)glycine and salts thereof, and 1/200 to about 5/1 when (B) is fatty acid salt.

Recent advances in molecular biology and taxonomy have provided for the distinction of photosynthetic procaryotic bacteria versus eucaryotic algae. In the past literature, the term "blue-green algae" made reference to a group of microorganisms which possessed chlorophyll and appeared blue-green in color. More recent textbooks on microbiology (*Biology of Microorganisms*, T D Brock, D W Smith, and MT Madigan, Prentice Hall, Inc. 1984) have distinguished these organisms from eucaryotic algae, such as the green algae, and considered them to be most appropriately classified as "blue-green bacteria" or "cyanobacteria". This distinction is made since the cell architecture more closely resembles the procaryotic bacteria than eucaryotic algae. Therefore, we refer herein to photosynthetic blue-green microorganisms as cyanobacteria or blue-green bacteria.

The following examples represent just a few of the many uses and compounds of the invention. They are intended to be illustrative but not limiting. Various modifications, alternatives, and improvements should become apparent to those skilled in the art without departing from the spirit and scope of the invention.

EXAMPLES

A. General Procedure

MIC values represent the Minimum Inhibitory Concentration. This is defined as the lowest level of compound required to completely inhibit (repress) the growth of a given organism.

A synergistic effect is defined as the response of two variables which is greater than the sum of both parts alone. Synergy was determined from combination studies with two compounds by the method of calculation described by F. C. Kull, P. C. Eisman, H. D. Sylwestrowicz and R. K. Mayer, *Applied Microbiology* 9,538 (1961):

$$\frac{Q_a}{Q_A} + \frac{Q_b}{Q_B} = \text{synergism index } (SI)$$

where:
- $Q_A$ = quantity of compound A, acting alone, producing an end point (MIC)
- $Q_a$ = quantity of compound A, in mixture, which inhibits growth
- $Q_B$ = quantity of compound B, acting alone, producing an end point (MIC)
- $Q_b$ = quantity of compound B, in mixture, which inhibits growth The following SI values may be attained:
- SI > 1 represents antagonistic effect,
- SI = 1 represents additive effect,
- SI < 1 represents synergy.

Efficacy studies were conducted on a variety of microorganisms with oxyfluorfen/commercial biocide mixtures. The MIC studies were conducted using microtiter plate assays. In this method, a wide range of concentrations was tested by preparing two-fold serial dilutions of the compound in 96-well plastic microtiter plates. All liquid media transfers were performed with calibrated single or multichannel digital pipetters. Stock solutions of compounds were prepared in appropriate solvents and dispensed to the growth medium. All subsequent dilutions in plates were made using the desired growth medium; total volume of liquid in each well was 100 μl. Each plate contained a concentration of both compounds made by serially titrating equal volumes of liquids in two directions in the microtiter plate. Each plate contained a control row for each combination (one component only), hence, the individual compound MIC values were also determined.

The pure cultures used in this study were obtained from the Culture Collection of Algae at the University of Texas at Austin (UTEX) and are listed in Table 1. Mixed cooling tower cultures were obtained from surface scrapings of industrial cooling towers. Microorganisms used as inocula were cultured in shaken liquid culture (Bristol's medium, pH 7.0, 25 C., *Journal of*

Phycology, 23s, 1-47, 1987 or Modified Allen's Media Formulation, described below) for one week or as needed to attain a desired cell mass. The cultures were then inoculated into the microtiter plates using a 96-prong multiple inoculator (5 μl inoculum); each well received a standard suspension of biomass (5% inoculum). Plates were incubated at 25° C. under constant illumination (500 ft candles). The extent of growth was determined under low magnification with the aid of microtiter plate reader. Growth in each well was monitored periodically and growth/no-growth was recorded after 14 or 21 days. Results of each study were evaluated by calculating synergy index values (SI, previously described).

TABLE 1

Pure Cultures of Green Algae and Cyanobacteria Used in MIC and Combination Studies

| Organisms | UTEX ID # |
|---|---|
| Green Algae (Chlorophyceae) | |
| Chlorella pyrenoidosa | 1230 |
| Scenedesmus quadricauda | 614 |
| Blue-Green Bacteria (Cyanobacteria) | |
| Anabaena flos-aquae | 1444 |
| Nostoc commune | 584 |

B. Preparation of Modified Allen's Media Formulation (pH 6.3)

| Component | Concentration (mg/l) |
|---|---|
| $NaNO_3$ | 250 |
| $CaCl_2(2H_2O)$ | 31 |
| $MgSO_4(7H_2O)$ | 75 |
| NaCl | 25 |
| $KH_2PO_4$ | 175 |
| $K_2HPO_4$ | 75 |
| $FeCl_3(6H_2O)$ | 7.5 |
| $Na_2(EDTA)$ | 10.3 |
| $Na_2B_4O_7(10H_2O)$ | 2.25 |
| $MnCl_2(4H_2O)$ | 0.90 |
| $ZnCl_2(7H_2O)$ | 0.11 |
| $CuCl_2(2H_2O)$ | 0.025 |
| $Na_2MoO_4(2H_2O)$ | 0.015 |
| $VOSO_4(2H_2O)$ | 0.015 |
| $CoCl_2(6H_2O)$ | 0.005 |

Descriptions of oxyfluorfen and the commercial biocides which were used in the combination efficacy studies are provided below:

oxyfluorfen: 98% technical grade
sodium hypochlorite: aqueous bleach, 5.25% active ingredient
halodialkylhydantoin: 60% 3-bromo-1-chloro-5,5-dimethylhydantoin, 27% 1,3-dichloro-5,5-dimethylhydantion, 11% 1,3-dichloro-5-ethyl-5-methylhydantoin mixture
n-alkyl dimethyl benzylammonium chloride: Hyamine ® 3500 surfactant, n-($C_{12}$-$C_{16}$)alkyl, 50% active ingredient
2,2-dibromo-3-nitrilopropionamide: DBNPA, 20% active ingredient
2-bromo-2-nitro-1,3-propanediol: BNPD, bronopol, Myacide ® AS biocide
poly[oxyethylene(dimethylimino)ethylene(dimethylimino)ethylene dichloride]: WSCP ® biocide, 60% active ingredient
3-iodo-2-propynylbutylcarbamate: Polyphase ® AF1 biocide, 40% active ingredient
sodium N-methyldithiocarbamate: Vapam ® fungicide
zinc bis(dimethyldithiocarbamate): ziram
p-tolyldiiodomethylsulfone: Amical ® 48 fungicide
3-(3,4-dichlorophenyl)-1,1-dimethylurea: diuron
fatty acid salt: potassium salt of mixed fatty acids, 2.0% active ingredient in water/alcohol mixture, Safer ® Insecticide Soap available from Safer ®, Inc., Newton, Me.
N-(phosphonomethyl)glycine: glyphosate, isopropylamine salt (Roundup ® herbicide)

EXAMPLE 1

Using a pure culture of Chlorella pyrenoidosa (green alga), various combinations of oxyfluorfen (acetone solution) and Compound B (in water) were subjected to MIC determinations in modified Allen's medium. In this example, Compound (A) is oxyfluorfen and Compound (B) is sodium hypochlorite. Concentrations ($Q_a$, $Q_b$) are expressed in ppm in this example and all the following examples.

| $Q_a$ | $Q_b$ | $Q_a/Q_b$ | SI |
|---|---|---|---|
| 0 | 2.0 ($Q_B$) | — | 1.0 |
| 0.094 | 1.0 | 1/11 | 0.56 |
| 0.187 | 1.0 | 1/5 | 0.62 |
| 0.375 | 1.0 | 1/3 | 0.75 |
| 1.5 ($Q_A$) | 0 | — | 1.0 |

EXAMPLE 2

Using a pure culture of Chlorella pyrenoidosa (green alga), various combinations of oxyfluorfen (acetone solution) and Compound B (in water) were subjected to MIC determinations in modified Allen's medium. In this example, Compound (A) is oxyfluorfen and Compound (B) is halodialkylhydantoin.

| $Q_a$ | $Q_b$ | $Q_a/Q_b$ | SI |
|---|---|---|---|
| 0 | 2.0 ($Q_B$) | — | 1.0 |
| 0.023 | 1.0 | 1/43 | 0.56 |
| 0.047 | 1.0 | 1/21 | 0.62 |
| 0.094 | 1.0 | 1/11 | 0.75 |
| 0.187 | 0.50 | 1/3 | 0.75 |
| 0.187 | 0.25 | 1/1.3 | 0.62 |
| 0.187 | 0.125 | 1.5/1 | 0.56 |
| 0.375 ($Q_A$) | 0 | — | 1.0 |

EXAMPLE 3

Using a pure culture of Chlorella pyrenoidosa (green alga), various combinations of oxyfluorfen (acetone solution) and Compound B (in water) were subjected to MIC determinations in modified Allen's medium. In this example, Compound (A) is oxyfluorfen and Compound (B) is n-alkyl dimethyl benzylammonium chloride.

| $Q_a$ | $Q_b$ | $Q_a/Q_b$ | SI |
|---|---|---|---|
| 0 | 3.0 ($Q_B$) | — | 1.0 |
| 0.047 | 1.5 | 1/32 | 0.62 |
| 0.094 | 1.5 | 1/16 | 0.75 |
| 0.188 | 0.75 | 1/4 | 0.75 |
| 0.375 ($Q_A$) | 0 | — | 1.0 |

EXAMPLE 4

Using a pure culture of Chlorella pyrenoidosa (green alga), various combinations of oxyfluorfen (acetone solution) and Compound B (in water) were subjected to MIC determinations in modified Allen's medium. In this example, Compound (A) is oxyfluorfen and Compound (B) is 2,2-dibromo-3-nitrilopropionamide.

| $Q_a$ | $Q_b$ | $Q_a/Q_b$ | SI |
|---|---|---|---|
| 0 | 4.0 ($Q_B$) | — | 1.0 |
| 0.004 | 2.0 | 1/500 | 0.50 |
| 0.008 | 2.0 | 1/250 | 0.51 |
| 0.016 | 2.0 | 1/125 | 0.52 |
| 0.031 | 2.0 | 1/64 | 0.53 |
| 0.063 | 2.0 | 1/32 | 0.56 |
| 0.125 | 2.0 | 1/16 | 0.62 |
| 0.25 | 2.0 | 1/8 | 0.75 |
| 0.063 | 1.0 | 1/16 | 0.31 |
| 0.125 | 1.0 | 1/8 | 0.38 |
| 0.25 | 1.0 | 1/4 | 0.50 |
| 0.50 | 1.0 | 1/2 | 0.75 |
| 0.25 | 0.5 | 1/2 | 0.38 |
| 0.50 | 0.5 | 1/1 | 0.62 |
| 1.0 ($Q_A$) | 0 | — | 1.0 |

EXAMPLE 5

Using a pure culture of *Scenedesmus quadricauda* (green alga), various combinations of oxyfluorfen (acetone solution) and Compound B (in water) were subjected to MIC determinations in modified Allen's medium. In this example, Compound (A) is oxyfluorfen and Compound B is 2-bromo-2-nitro-1,3-propanediol.

| $Q_a$ | $Q_b$ | $Q_a/Q_b$ | SI |
|---|---|---|---|
| 0 | 7.5 ($Q_B$) | — | 1.0 |
| 0.038 | 3.75 | 1/100 | 0.62 |
| 0.075 | 3.75 | 1/50 | 0.75 |
| 0.30 ($Q_A$) | 0 | — | 1.0 |

EXAMPLE 6

Using a pure culture of *Scenedesmus quadricauda* (green alga), various combinations of oxyfluorfen (acetone solution) and Compound B (in water) were subjected to MIC determinations in modified Allen's medium. In this example, Compound (A) is oxyfluorfen and Compound (B) is poly[oxyethylene(dimethylimino)ethylene(dimethylimino)ethylene dichloride].

| $Q_a$ | $Q_b$ | $Q_a/Q_b$ | SI |
|---|---|---|---|
| 0 | 1.50 ($Q_B$) | — | 1.0 |
| 0.019 | 0.75 | 1/40 | 0.57 |
| 0.038 | 0.75 | 1/20 | 0.62 |
| 0.075 | 0.75 | 1/10 | 0.75 |
| 0.30 ($Q_A$) | 0 | — | 1.0 |

EXAMPLE 7

Using a pure culture of *Chlorella pyrenoidosa* (green alga), various combinations of oxyfluorfen (acetone solution) and Compound B (in acetone) were subjected to MIC determinations in modified Allen's medium. In this example, Compound (A) is oxyfluorfen and Compound (B) is 3-iodo-2-propynylbutylcarbamate.

| $Q_a$ | $Q_b$ | $Q_a/Q_b$ | SI |
|---|---|---|---|
| 0 | 8.0 ($Q_B$) | — | 1.0 |
| 0.047 | 4.0 | 1/85 | 0.56 |
| 0.094 | 4.0 | 1/43 | 0.62 |
| 0.188 | 4.0 | 1/21 | 0.75 |
| 0.094 | 2.0 | 1/21 | 0.38 |
| 0.188 | 2.0 | 1/11 | 0.50 |
| 0.375 | 2.0 | 1/5 | 0.75 |
| 0.75 ($Q_A$) | 0 | — | 1.0 |

EXAMPLE 8

Using a pure culture of *Anabaena flos-aquae* (blue-green bacterium), various combinations of oxyfluorfen (acetone solution) and Compound B were subjected to MIC determinations in modified Allen's medium. In this example, Compound (A) is oxyfluorfen and Compound (B) is sodium N-methyldithiocarbamate.

| $Q_a$ | $Q_b$ | $Q_a/Q_b$ | SI |
|---|---|---|---|
| 0 | 62.5 ($Q_B$) | — | 1.0 |
| 0.49 | 31.25 | 1/64 | <0.51 |
| 0.98 | 31.25 | 1/32 | <0.51 |
| 1.95 | 31.25 | 1/16 | <0.51 |
| 3.9 | 31.25 | 1/8 | <0.51 |
| 7.8 | 31.25 | 1/4 | <0.52 |
| 15.6 | 31.25 | 1/2 | <0.53 |
| 31.2 | 31.25 | 1/1 | <0.56 |
| 62.5 | 31.25 | 2/1 | <0.63 |
| 125 | 31.25 | 4/1 | <0.75 |
| 250 | 15.6 | 16/1 | <0.75 |
| >500 ($Q_A$) | 0 | — | 1.0 |

EXAMPLE 9

Using a pure culture of *Nostoc commune* (blue-green bacterium), various combinations of oxyfluorfen (acetone solution) and Compound B were subjected to MIC determinations in modified Allen's medium. In this example, Compound (A) is oxyfluorfen and Compound (B) is sodium N-methyldithiocarbamate.

| $Q_a$ | $Q_b$ | $Q_a/Q_b$ | SI |
|---|---|---|---|
| 0 | 3.9 ($Q_B$) | — | 1.0 |
| 250 | 1.95 | 128/1 | <0.75 |
| >1000 ($Q_A$) | 0 | — | 1.0 |

EXAMPLE 10

Using a pure culture of *Anabaena flos-aquae* (blue-green bacterium), various combinations of oxyfluorfen (acetone solution) and Compound B were subjected to MIC determinations in modified Allen's medium. In this example, Compound (A) is oxyfluorfen and Compound (B) is zinc bis(dimethyldithiocarbamate).

| $Q_a$ | $Q_b$ | $Q_a/Q_b$ | SI |
|---|---|---|---|
| 0 | 125 ($Q_B$) | — | 1.0 |
| 0.49 | 62.5 | 1/128 | <0.51 |
| 1 | 62.5 | 1/64 | <0.51 |
| 2 | 62.5 | 1/32 | <0.51 |
| 3.9 | 62.5 | 1/16 | <0.51 |
| 7.8 | 62.5 | 1/8 | <0.52 |
| 15.6 | 62.5 | 1/4 | <0.53 |
| 31.2 | 62.5 | 1/2 | <0.56 |
| 62.5 | 62.5 | 1/1 | <0.63 |
| 125 | 62.5 | 2/1 | <0.75 |
| 7.8 | 31.25 | 1/4 | <0.27 |
| 15.6 | 31.25 | 1/2 | <0.28 |
| 31.2 | 31.25 | 1/1 | <0.31 |
| 62.5 | 31.25 | 2/1 | <0.33 |
| 125 | 31.25 | 4/1 | <0.50 |
| 250 | 31.25 | 8/1 | <0.75 |
| 7.8 | 15.6 | 1/2 | <0.14 |
| 15.6 | 15.6 | 1/1 | <0.16 |

-continued

| $Q_a$ | $Q_b$ | $Q_a/Q_b$ | SI |
|---|---|---|---|
| 31.2 | 15.6 | 2/1 | <0.19 |
| 62.5 | 15.6 | 4/1 | <0.25 |
| 125 | 15.6 | 8/1 | <0.38 |
| 250 | 15.6 | 16/1 | <0.63 |
| 7.8 | 7.8 | 1/1 | <0.08 |
| 15.6 | 7.8 | 2/1 | <0.09 |
| 31.2 | 7.8 | 4/1 | <0.12 |
| 62.5 | 7.8 | 8/1 | <0.19 |
| 125 | 7.8 | 16/1 | <0.31 |
| 250 | 7.8 | 32/1 | <0.56 |
| >500 ($Q_A$) | 0 | — | 1.0 |

EXAMPLE 11

Using a pure culture of *Anabaena flos-aquae* (blue-green bacterium), various combinations of oxyfluorfen (acetone solution) and Compound B were subjected to MIC determinations in modified Allen's medium. In this example, Compound (A) is oxyfluorfen and Compound (B) is p-tolyldiiodomethylsulfone.

| $Q_a$ | $Q_b$ | $Q_a/Q_b$ | SI |
|---|---|---|---|
| 0 | 31.25 ($Q_B$) | — | 1.0 |
| 62.5 | 15.6 | 4/1 | <0.63 |
| 125 | 15.6 | 8/1 | <0.75 |
| 125 | 7.8 | 16/1 | <0.5 |
| >500 ($Q_A$) | 0 | — | 1.0 |

EXAMPLE 12

Using a pure culture of *Anabaena flos-aquae* (blue-green bacterium), various combinations of oxyfluorfen (acetone solution) and Compound B were subjected to MIC determinations in modified Allen's medium. In this example, Compound (A) is oxyfluorfen and Compound (B) is 3-(3,4-dichlorophenyl)-1,1-dimethylurea.

| $Q_a$ | $Q_b$ | $Q_a/Q_b$ | SI |
|---|---|---|---|
| 0 | 15.6 ($Q_B$) | — | 1.0 |
| 2 | 7.8 | 1/4 | <0.51 |
| 4 | 7.8 | 1/2 | <0.51 |
| 8 | 7.8 | 1/1 | <0.52 |
| 16 | 7.8 | 2/1 | <0.53 |
| 31 | 7.8 | 4/1 | <0.56 |
| 62 | 7.8 | 8/1 | <0.62 |
| 125 | 7.8 | 16/1 | <0.75 |
| >500 ($Q_A$) | 0 | — | 1.0 |

EXAMPLE 13

Using a pure culture of *Anabaena flos-aquae* (blue-green bacterium), various combinations of oxyfluorfen (acetone solution) and Compound B were subjected to MIC determinations in modified Allen's medium. In this example, Compound (A) is oxyfluorfen and Compound (B) is fatty acid salt.

| $Q_a$ | $Q_b$ | $Q_a/Q_b$ | SI |
|---|---|---|---|
| 0 | 500 ($Q_B$) | — | 1.0 |
| 2 | 250 | 1/128 | <0.51 |
| 3.9 | 250 | 1/64 | <0.51 |
| 7.8 | 250 | 1/32 | <0.52 |
| 15.6 | 250 | 1/16 | <0.53 |
| 31.2 | 250 | 1/8 | <0.56 |
| 62.5 | 250 | 1/4 | <0.63 |
| 125 | 250 | 1/2 | <0.75 |
| 2 | 125 | 1/64 | <0.26 |
| 3.9 | 125 | 1/32 | <0.26 |
| 7.8 | 125 | 1/16 | <0.27 |
| 15.6 | 125 | 1/8 | <0.28 |
| 31.2 | 125 | 1/4 | <0.31 |
| 62.5 | 125 | 1/2 | <0.33 |
| 125 | 125 | 1/1 | <0.50 |
| 250 | 125 | 2/1 | <0.75 |
| >500 ($Q_A$) | 0 | — | 1.0 |

EXAMPLE 14

Using a pure culture of *Anabaena flos-aquae* (blue-green bacterium), various combinations of oxyfluorfen (acetone solution) and Compound B were subjected to MIC determinations in modified Allen's medium. In this example, Compound (A) is oxyfluorfen and Compound (B) is N-(phosphonomethyl)glycine.

| $Q_a$ | $Q_b$ | $Q_a/Q_b$ | SI |
|---|---|---|---|
| 0 | 15.6 ($Q_B$) | — | 1.0 |
| 15.6 | 7.8 | 2/1 | <0.53 |
| 31.2 | 7.8 | 4/1 | <0.56 |
| 62.5 | 7.8 | 8/1 | <0.63 |
| 125 | 7.8 | 16/1 | <0.75 |
| >500 ($Q_A$) | 0 | — | 1.0 |

EXAMPLE 15 (Comparative)

Using pure cultures of *Chlorella pyrenoidosa*, various combinations of oxyfluorfen (acetone solution) and different commercial biocides representing Compound B were subjected to MIC determinations in modified Allen's medium. In all of the listed cases no synergy was detected for these combinations at or below the concentrations (expressed as ppm) of oxyfluorfen and Compound (B) indicated.

| Compound B | Oxyfluorfen/Compound B Ratio |
|---|---|
| Bis(tributyltin)oxide (TBTO): | 0.5/16 |
| TBTO/Quat (TBTO + n-alkyl dimethyl benzylammonium chloride): 15% active | 0.5/1 |
| Glutaraldehyde (1,5-pentanedial): 50% active | 0.5/31 |
| Dodecylguanidine-HCl (DGH): Cytox ® 2050 biocide, 12.5% active | 0.5/2 |
| N-(4-Bromo-2-methylphenyl)-2-chloroacetamide: Cosan ® 528W biocide, 40% active | 0.5/8 |
| Tetrahydroisophthalonitrile: Nopcocide ® N96 biocide | 0.5/0.5 |
| N-(Trichloromethylthio)phthalimide: Fungitrol ® biocide, 88% active | 0.5/0.8 |
| N,N-Dimethyl-N'-phenyl-N'-(fluorodichloromethylthio)sulfamide: Preventol ® A4 biocide | 0.5/2 |
| Methylene-bis(thiocyanate) | 0.5/0.8 |
| Disodium ethylenebis(dithiocarbamate): Dithane ® D-14 fungicide | 0.5/2 |
| 2-Methylthio-4-(1,2-dimethylpropyl amino)-6-ethylamino-1,3,5-triazine: dimethametryn, Mogul ® AG-439 biocide | 0.5/0.01 |

We claim:

1. An article comprising a swimming pool liner comprised of an algae resistant plastic composition comprising an effective amount of a microbicidal composition useful for controlling algae comprising a synergistic mixture of (A) a diphenylether compound of the formula

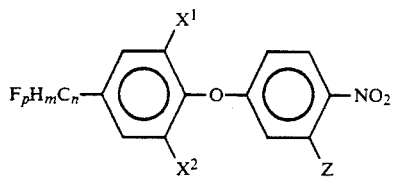

wherein
- $X^1$, $X^2$ are independently selected from the group consisting of hydrogen, halogen, trihalomethyl, cyano, and $(C_1-C_4)$alkyl;
- Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or lower alkyl amino, RO in which R represents a hydrogen atom or an ester bonded acid radical of an inorganic or organic oxyacid;
- p is an integer from 1 to $2n+1$;
- m is an integer of 0 to $2n$;
- n is an integer of 1 to 5;
- $m+p=2n+1$ and (B) a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly[oxyethylene(dimethylimino)ethylene(dimethylimino)ethylene dichloride], 3-iodo-2-propynylbutylcarbamate, sodium N-methyldithiocarbamate, zinc bis(dimethyldithiocarbamate), p-tolyldiiodomethylsulfone and fatty acid salt wherein the ratio of (A) to (B) is in a range of from about 1/1000 to about 200/1 by weight.

2. An article comprising plastic coated with a coating composition comprising from about 0.1 PPM to about 2 percent by weight of a microbicidal composition useful for controlling algae comprising a synergistic mixture of (A) a diphenylether compound of the formula

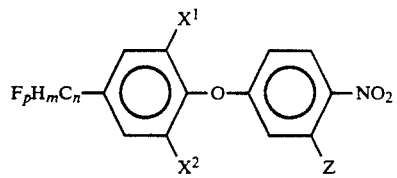

wherein
- $X^1$, $X^2$ are independently selected from the group consisting of hydrogen, halogen, trihalomethyl, cyano, and $(C_1-C_4)$alkyl;
- Z is selected from the group consisting of hydrogen, halogen, cyano, carboxy or salt thereof, lower alkylthio, lower carbalkoxy, lower carboxyalkyl, lower carbalkoxyalkyl, lower carbalkoxyalkoxycarbonyl, lower carbalkoxyalkoxy, lower alkoxy, lower cycloalkoxy, lower alkenyl, lower alkyl, lower cycloalkyl, unsubstituted or lower alkyl amino, RO in which R represents a hydrogen atom or an ester bonded acid radical of an inorganic or organic oxyacid;
- p is an integer from 1 to $2n+1$;
- m is an integer of 0 to $2n$;
- n is an integer of 1 to 5;
- $m+p=2n+1$ and (B) a material selected from the group consisting of sodium hypochlorite, halodialkylhydantoin, n-alkyl dimethyl benzylammonium chloride, 2,2-dibromo-3-nitrilopropionamide, 2-bromo-2-nitro-1,3-propanediol, poly, 3-iodo-2-propynylbutylcarbamate, sodium N-methyldithiocarbamate, zinc bis(dimethyldithiocarbamate), p-tolyldiiodomethylsulfone and fatty acid salt wherein the ratio (A) to (B) is in a range of from about 1/1000 to about 200/1 by weight.

* * * * *